US009799757B2

(12) United States Patent
Gridelet et al.

(10) Patent No.: US 9,799,757 B2
(45) Date of Patent: Oct. 24, 2017

(54) PN JUNCTION CHEMICAL SENSOR

(75) Inventors: Evelyne Gridelet, Omal (BE); Almudena Huerta, Madrid (ES); Pierre Goarin, Graz (AT); Jan Sonsky, Leuven (BE)

(73) Assignee: NXP B.V., Eindhoven (NL)

(*) Notice: Subject to any disclaimer, the term of this patent is extended or adjusted under 35 U.S.C. 154(b) by 1641 days.

(21) Appl. No.: 12/922,665

(22) PCT Filed: Mar. 9, 2009

(86) PCT No.: PCT/IB2009/050976
§ 371 (c)(1),
(2), (4) Date: May 13, 2011

(87) PCT Pub. No.: WO2009/113013
PCT Pub. Date: Sep. 17, 2009

(65) Prior Publication Data
US 2011/0204872 A1    Aug. 25, 2011

(30) Foreign Application Priority Data

Mar. 14, 2008 (EP) .................................. 08102607

(51) Int. Cl.
G01N 27/00 (2006.01)
H01L 29/739 (2006.01)
G01N 27/414 (2006.01)

(52) U.S. Cl.
CPC ..... H01L 29/7391 (2013.01); G01N 27/4145 (2013.01)

(58) Field of Classification Search
CPC .... G01N 27/4145; G01N 27/12; G01N 27/00; H01L 29/7391; H01L 29/66; H01L 31/118; H01L 21/3242; H01L 21/28211
(Continued)

(56) References Cited

U.S. PATENT DOCUMENTS 4,103,227 A    7/1978 Zemel
5,394,735 A    3/1995 Fang et al.
(Continued)

FOREIGN PATENT DOCUMENTS

WO    2006/136979 A2    12/2006

OTHER PUBLICATIONS

Inezedy, Janos, et al; "Compendium of Analytical Nomenclature—Definitive Rules 1997—Chapter 8.3.3.4", reprinted from http://old.iupac.org/publications/analytical_compendium/ (2000).
Kang, C. et al; "Characteristics of n+-Psi-p+ Humidity Sensors Using Porous Silicon Diaphragm," J. of the Korean Physical Society, vol. 39, pp. S88-S91 (Dec. 2001).
(Continued)

*Primary Examiner* — Son Le
*Assistant Examiner* — Brent J Andrews

(57) ABSTRACT

A sensor device (100, 2800) for detecting particles, the sensor device (100, 2800) comprising a substrate (102), a first doped region (104) formed in the substrate (102) by a first dopant of a first type of conductivity, a second doped region (106, 150) formed in the substrate (102) by a second dopant of a second type of conductivity which differs from the first type of conductivity, a depletion region (108) at a junction between the first doped region (104) and the second doped region (106, 150), a sensor active region (110) adapted to influence a property of the depletion region (108) in the presence of the particles, and a detection unit (112) adapted to detect the particles based on an electric measurement performed upon application of a predetermined reference voltage between the first doped region (104) and the second doped region (106, 150), the electric measurement being indicative of the presence of the particles in the sensor active region (110).

22 Claims, 4 Drawing Sheets

(58) Field of Classification Search
USPC ............ 257/414, 429, E29.166, E31.089; 324/71.1

See application file for complete search history.

(56) References Cited

U.S. PATENT DOCUMENTS

| | | | |
|---|---|---|---|
| 5,434,442 A | | 7/1995 | Lesk et al. |
| 5,457,322 A | * | 10/1995 | Kitaguchi et al. ....... 250/370.06 |
| 5,466,348 A | * | 11/1995 | Holm-Kennedy ............ 205/775 |
| 5,691,558 A | | 11/1997 | Davies |
| 7,692,219 B1 | * | 4/2010 | Holm-Kennedy ............ 257/253 |
| 7,897,478 B2 | | 3/2011 | Sonsky |
| 2003/0193073 A1 | * | 10/2003 | Tuller et al. .................. 257/414 |
| 2005/0199970 A1 | * | 9/2005 | Monfray et al. ............. 257/414 |
| 2006/0118903 A1 | * | 6/2006 | Cahen et al. ................ 257/494 |
| 2008/0197423 A1 | * | 8/2008 | Oppermann .................. 257/386 |
| 2009/0072319 A1 | * | 3/2009 | Sonsky et al. ............... 257/368 |
| 2009/0160024 A1 | * | 6/2009 | Chi ............................... 257/536 |
| 2009/0250696 A1 | * | 10/2009 | Silver et al. .................... 257/46 |
| 2010/0052080 A1 | | 3/2010 | Tello et al. |
| 2010/0066348 A1 | * | 3/2010 | Merz et al. ................. 324/71.1 |

OTHER PUBLICATIONS

Nakashima, K. et al. "A New Type of SiC Gas Sensor With a pn-Junction Structure," Materials Science Forum; vols. 389-393, pp. 1427-1430 (2002).

Sato, T. et al. "Fabrication of Silicon-On-Nothing Structure by Substrate Engineering Using the Empty-Space-In-Silicon Formation Technique," Japanese J. of Applied Phys., vol. 43, No. 1, pp. 12-18 (2004).

Poghossian, A. et al. "Detecting Both Physical and (Bio-) Chemical Parameters by Means of Isfet Devices" Electroanalysis 2004, 16, No. 22; pp. 1863-1872 (2004).

Sonsky, J. et al. "Dielectric Resurf: Breakdown Voltage Control by STI Layout in Standard CMOS," IEEE Interl Electron Devices Meeting, IEDM Technical Digest (Dec. 2005).

Raissi, F., et al; "Room-Temperature Gas-Sensing Ability of PtSi/ Porous Si Schottky Junctions," IEEE Sensors Journal, vol. 6, No. 1, pp. 146-150 (Feb. 2006).

Barillaro, G., et al. "p+-n. Diodes With a Lateral Porous Layer As Gas Sensors," Physica Status Solidi (a), vol. 204, No. 5, pp. 1399-1403 (2007).

International Search Report and Written Opinion for Int'l. Patent Appln. No. PCT/IB2009/050976.

* cited by examiner

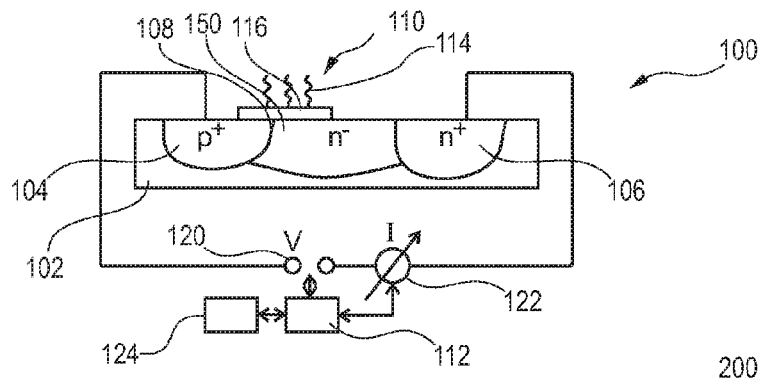
Fig. 1
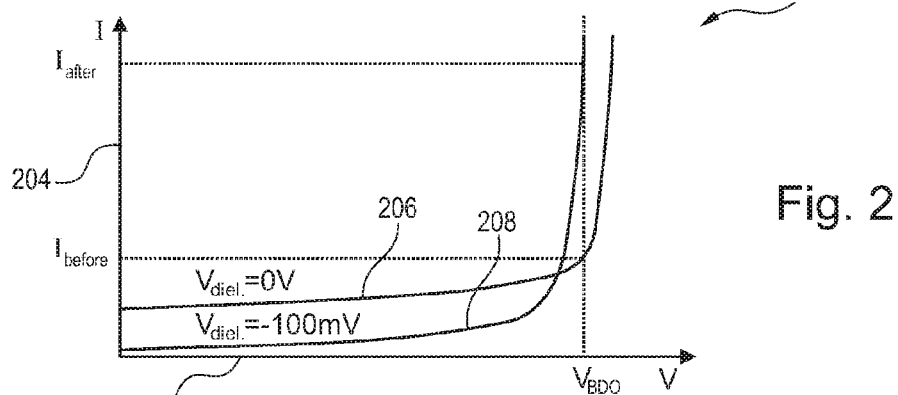
Fig. 2
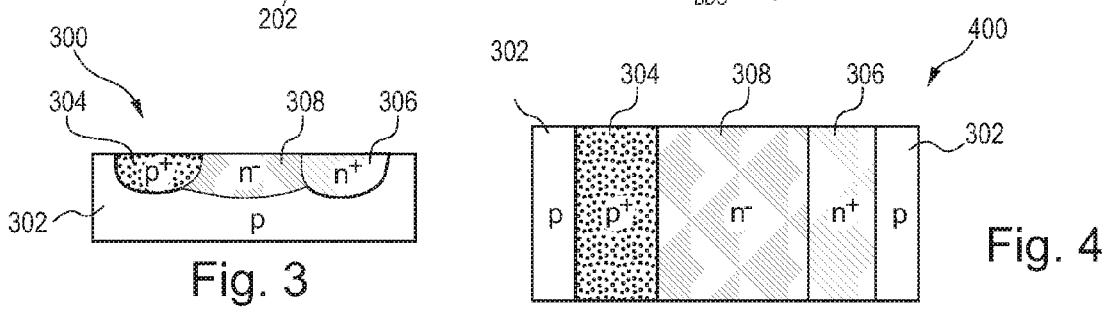
Fig. 3
Fig. 4
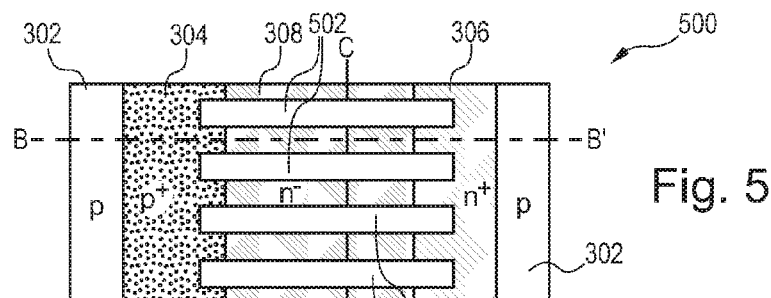
Fig. 5
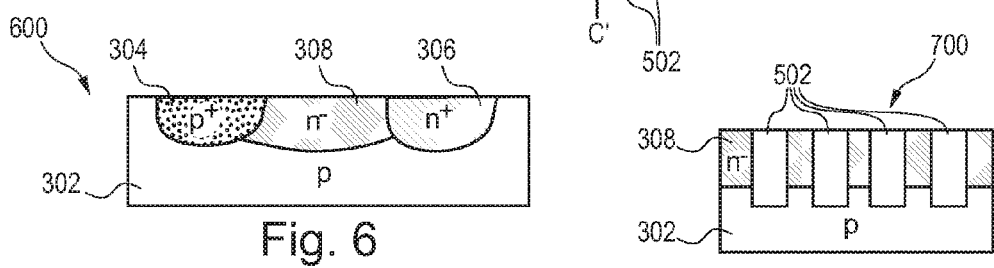
Fig. 6
Fig. 7

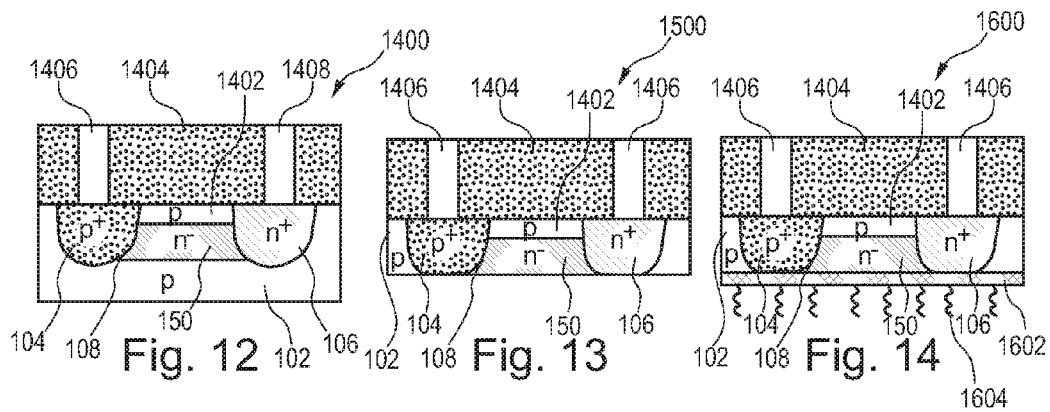
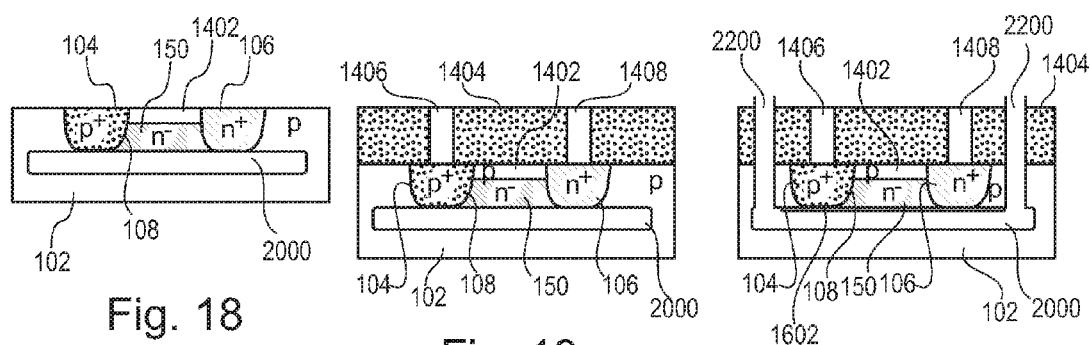
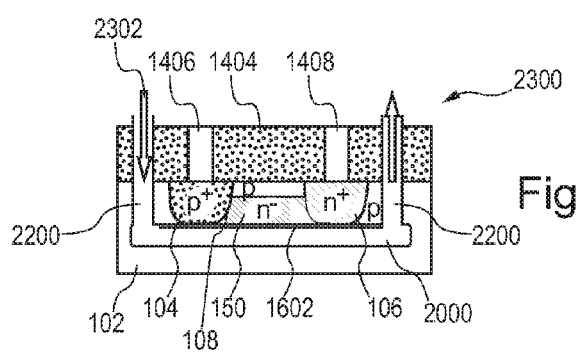

PN JUNCTION CHEMICAL SENSOR

FIELD OF THE INVENTION

The invention relates to a sensor device.

Moreover, the invention relates to a method of detecting particles.

BACKGROUND OF THE INVENTION

A biosensor may be denoted as a device to be used for the detection of an analyte that combines a biological component with a physicochemical or physical detector component.

For instance, a biosensor may be based on the phenomenon that capture particles immobilized on a surface of a biosensor, may selectively attach with target particles in a fluidic sample, for instance when an antibody-binding fragment of an antibody or the sequence of a DNA single strand as a capture particle fits to a corresponding sequence or structure of a target particle. When such attachment or sensor events occur at the sensor surface, this may change the electrical properties of the surface, which can be detected as the sensor event.

G. Barillaro, A. Diligenti, L. M. Strambini, "$p^+$-n diodes with a lateral porous layer as gas sensors", Physica Status Solidi (a), Volume 204, Issue 5, pp. 1399-1403 discloses an integrated $p^+$-n diode, diffused on a crystalline substrate and provided with a thin adsorbing porous layer as gas sensor. The sensor can be integrated by using an industrial CMOS process due to the fact that the porous film formation is the last process step. The sensitivity to isopropanol vapors has been investigated by measuring both the forward and reverse current of the diode as a function of the vapor concentration. The current variations, up to two orders of magnitude, could be explained by assuming that the adsorption of particles in the porous layer and their interaction with localized states modify the band structure of the crystalline diode at the interface with the porous silicon, and in turn its current. Another sensor feature is that the value of the reverse current variation, induced by isopropanol vapors, depends on the voltage, so that the sensitivity can be settled by simply changing the reverse voltage itself.

OBJECT AND SUMMARY OF THE INVENTION

It is an object of the invention to provide an accurate system for detecting particles.

In order to achieve the object defined above, a sensor device and a method of detecting particles according to the independent claims are provided.

According to an exemplary embodiment of the invention, a sensor device for detecting particles is provided, the sensor device comprising a substrate, a first doped region formed in the substrate by a first dopant of a first type of conductivity, a second doped region formed in the substrate by a second dopant of a second type of conductivity which differs from the first type of conductivity, a depletion region at a junction between the first doped region and the second doped region, a sensor active region adapted to influence a property (for instance a size, thereby influencing the electric characteristic of the sensor device) of the depletion region in the presence of the particles, and a detection unit adapted to detect the particles based on an electric measurement performed upon application of a predetermined reference voltage (for instance a voltage at or close to the breakdown voltage of the diode structure formed by the doped regions and the intermediate depletion region) between the first doped region and the second doped region, the electric measurement being indicative of the presence of the particles in the sensor active region.

According to another exemplary embodiment of the invention, a method of detecting particles is provided, the method comprising providing a depletion region at a junction between a first doped region formed in a substrate by a first dopant of a first type of conductivity and a second doped region formed in a substrate by a second dopant of a second type of conductivity which differs from the first type of conductivity, influencing a property of the depletion region by the presence of the particles, and detecting the particles based on an electric measurement performed upon application of a predetermined reference voltage (for instance a voltage at or close to the breakdown voltage of the diode structure formed by the doped regions and the intermediate depletion region) between the first doped region and the second doped region, the electric measurement being indicative of the presence of the particles in the sensor active region.

The term "biosensor" may particularly denote any device that may be used for the detection of a component of an analyte comprising biological particles such as DNA, RNA, proteins, enzymes, cells, bacteria, virus, etc. A biosensor may combine a biological component (for instance capture particles at a sensor active surface capable of detecting particles) with a physicochemical or physical detector component (for instance a diode having a current-voltage characteristic which is modifiable by a sensor event).

The term "sensor chip" may particularly denote that a sensor is formed as an integrated circuit, that is to say as an electronic chip, particularly in semiconductor technology, more particularly in silicon semiconductor technology, still more particularly in CMOS technology. A monolithically integrated sensor chip has the property of very small dimensions thanks to the use of micro-processing technology, and may therefore have a large spatial resolution and a high signal-to-noise ratio particularly when the dimensions of the sensor chip or more precisely of components thereof approach or reach the order of magnitude of micrometers or less, for instance in case of a biosensor reaching the dimensions of biological particles.

The term "sensor active region" may particularly denote an exposed region of a sensor which may be brought in interaction with a fluidic sample so that a detection event may occur in the sensor active region. In other words, the sensor active region may be the actual sensitive area of a sensor device, in which area processes take place which form the basis of the sensing. A corresponding sensing principle may be an electrical sensing principle (that is a change of the electric properties of the sensor active region or of the depletion region functionally coupled thereto).

The term "substrate" may denote any suitable material, such as a semiconductor, glass, plastic, etc. According to an exemplary embodiment, the term "substrate" may be used to define generally the elements for layers that underlie and/or overlie a layer or portions of interest. Also, the substrate may be any other base on which a layer is formed, for example a semiconductor wafer such as a silicon wafer or silicon chip. The substrate may be made of silicon doped with a lower doping concentration than the doping concentration of the first and second doped regions.

The term "fluidic sample" may particularly denote any subset of the phases of matter. Such fluids may include liquids, gases, plasmas and, to some extent, solids, as well as mixtures thereof. Examples for fluidic samples are DNA containing fluids, blood, interstitial fluid in subcutaneous tissue, muscle or brain tissue, urine or other body fluids. For instance, the fluidic sample may be a biological substance. Such a substance may comprise proteins, polypeptides, nucleic acids, DNA strands, etc.

The term "particle" may particularly denote a molecule, an organic molecule, a biological particle, DNA, RNA, a protein, an amino acid, a bead, a nano-bead, a nano-tube, etc.

The term "biological particles" may particularly denote any particles which play a significant role in biology or in biological or biochemical procedures, such as genes, DNA, RNA, proteins, enzymes, cells, bacteria, virus, etc.

The term "breakdown voltage" of a diode may particularly denote a value of an electric voltage measured at a specified electric current value in the electrical breakdown region of a semiconductor diode in reverse bias, that is to say a pn-junction having a charge carrier depletion between n-zone and p-zone. Electrical breakdown may be a large, usually abrupt, rise in electric current in the presence of a small increase in voltage. Such a behaviour around in a breakdown regime is shown in FIG. 2.

The term "depletion region" may particularly denote a region at a junction between two doped regions in which the net density of charge carriers (electrons or holes) is very small or close to zero. Such a depletion region may have a charge carrier density which is significantly smaller than a charge carrier density in the adjacent doped regions. The depletion region may be a depletion volume formed by a partial or complete compensation of charge carriers of different type of conductivity at a junction or direct connection between two doped regions.

According to an exemplary embodiment of the invention, a current value (or another electric signal) of a diode is sampled in response to the application of an electric reference voltage to the diode to detect the presence of particles in an adjacent sensor active region based on a characteristic impact of the presence of the particles on the properties of a depletion region of the diode which depletion region is brought in functional contact with the (particularly electrically charged) particles. When such a reference voltage is selected close to (for instance less than 10%, particularly less than 5%, more particularly less than 1% away from the breakdown voltage) or exactly at a breakdown voltage of the diode, a very sensitive sensor device can be obtained due to the large slope of a current-voltage curve of a diode around the breakdown voltage. Thus, only very small changes of the electric properties in an environment of the sensor diode may have an extremely strong impact on the sampled electric current value.

According to an exemplary embodiment of the invention, a system of detecting (for instance charged) particles is provided, the system comprising the provision of a semiconductor device of a p$^+$-region and an n$^+$-region (with or without an optional lowly doped p$^-$-region or n$^-$-region between the p$^+$-region and the n$^+$-region), wherein a depletion region may be provided at a resulting pn-junction, the provision of a dielectric contact element to the depletion region, which contact element may be adapted to contact (for instance charged) particles, the application of a particle to be detected to the contact element, and the detection of the particle based on a current value of the semiconductor device at a breakdown potential or close to a breakdown potential, wherein the semiconductor device may be operated in a reverse bias mode.

According to an exemplary embodiment of the invention, the reference or measurement voltage may be determined by one or two scans of a current-voltage curve, and then the real measurement may be done only at this voltage. Actually, a manufacturer may do the preliminary scans of a current-voltage dependency, and the measurement voltage may thus be set for all identical sensors. Taking this measure may be a significant advantage for products because a measurement at one point that gives a YES/NO answers is much easier than to perform a scan, which requires storing a row of points and doing some analyses. As a consequence, the detection may be performed by a change in the current of a diode at a given voltage, wherein this reference voltage may be close to or at the diode breakdown voltage.

Next, further exemplary embodiments of the sensor device will be explained. However, these embodiments also apply to the method.

The first doped region may be a p-doped region, and the second doped region may be an n-doped region. However, the doping scheme may be also vice versa, that is to say the first doped region may be an n-doped region and the second doped region may be a p-doped region. The concentration of dopants in the first and the second doped regions may be larger, particularly significantly larger, than a smaller concentration of dopants in the substrate. In the first doped region, the type of conductivity (for instance p-doping or n-doping) may be inverse to the doping characteristic of the second doped region (for instance n-doping or p-doping).

The sensor active region may be adapted to influence a breakdown voltage of a diode arrangement formed by the first doped region, the second doped region, and the depletion region in the presence of the particles. It has been recognized by the present inventors that the presence of electrically charged particles close to the sensor active region may result, via an impact on the size of the depletion region, in a shift of the breakdown characteristic of the diode configuration. Since a slope of the current-voltage curve close to the breakdown voltage is very high, a high sensitivity may be achieved.

The sensor active region may be formed directly on the depletion region. Thus, there may be a direct physical contact between the sensor active region and the depletion region. Sensor events which possibly occur in the sensor active region may therefore directly cause significant impact on the depletion region, and therefore particularly a significant impact on the electric current behaviour at the reference voltage. The sensor active region may alternatively be located close an edge of the depletion region. There may alternatively be an intermediate component or structure between the sensor active region and the depletion region. This structure may be an interconnect structure, a protective structure. It may be made of conductive or dielectric materials.

The sensor active region may include metal structures, dielectric structures, more particularly high-k dielectric structures, structures made of inorganic or organic molecules (like self-assembled monolayers).

The sensor active region may comprise capture particles adapted for attachment with the particles. For example, single stranded DNA may be immobilized at the sensor active region. In the presence of complementary DNA particles as the particles in a sample, an attachment (for instance a hybridization) event may occur so that double stranded DNA is formed at the sensor active region. Since DNA is usually electrically charged, the electric charge will influence the breakdown voltage behaviour by an impact on the depletion region, so that the presence of the particles can be detected electrically, in a qualitative or quantitative manner.

The sensor active region may comprise a dielectric layer between the capture particles and the depletion region. Such a dielectric layer can be optimized regarding the binding properties of capture particles and may ohmically decouple the depletion region from the fluidic sample.

The detection unit may be adapted to detect particles based on an evaluation of a property (particularly the size) of the depletion region by performing a measurement at or around the breakdown voltage, as the predetermined reference voltage, of the diode arrangement formed by the first doped region, the second doped region and the depletion region. Thus, the electric current may be measured at or close to the breakdown voltage, which is a reliable and sensitive indicator for the presence or absence of the particles.

The detection unit may be adapted for operating an arrangement formed by the first doped region, the second doped region and the depletion region with a reverse bias. Therefore, the diode may be biased electrically to be operated close to a breakdown voltage.

More particularly, the detection unit may be adapted for detecting the particles based on a shift of a breakdown voltage of an arrangement formed by the first doped region, the second doped region and the depletion region, with a reverse bias. When a sensor event occurs, the value of the breakdown voltage is modified so that, when measuring a current at a reference voltage which can be the breakdown voltage in the absence of the particles, the sensor event can be detected by a modified current value (see FIG. 2). When the characteristic curve has been measured in advance, the measured current may be an indicator regarding quality and/or quantity of the present particles.

More particularly, the detection unit may be adapted for detecting the particles by determining the predetermined voltage as a breakdown voltage of an arrangement formed by the first doped region, the second doped region and the depletion region in the absence of the particles. With such a method step, the reference breakdown voltage may be measured without the sample being present. Subsequently, an electric current may be measured at the breakdown voltage of the arrangement in the absence of the particles. Then, in the presence of the particles, an electric current value may be measured at the breakdown voltage of the arrangement determined in the absence of the particles. The two electric current values may then be compared and, if the two values differ, the presence of a sensor event may be recognized.

The sensor device may be adapted to detect electrically charged particles. The presence of electrically charged particles has a strong impact on the electric properties of the depletion region, therefore on the breakdown voltage or more precisely on the characteristic current-voltage dependency. However, alternatively, although higher order electric and/or magnetic multipole moments may be measured, for instance the presence of particles having an electrical dipole moment which may also have an impact on the electrical properties of the depletion regions.

The sensor device may comprise a plurality of trenches filled at least partially (that is entirely or partially to maintain a gap) with dielectric material and extending from the first doped region via the depletion region to the second doped region. In the presence of such trenches (see FIG. 10), it has been recognized that the breakdown voltage can be manipulated so that the measurement can be refined. WO 2006/136979 discloses such a structure comprising a trench, however, an exemplary embodiment of the present invention uses such a structure in completely another context than in case of WO 2006/136979.

More particularly, the sensor device may comprise an electrically conductive inlay in the dielectric material of at least a part of the plurality of trenches.

The plurality of trenches may be part of the sensor active region. Thus, the particles to be detected can be located or cumulated in the environment of the trenches.

The sensor device may be adapted in a manner that a fluidic sample including the particles is free from a contact with electrical connections of the sensor device. For instance, this can be achieved by providing access of a fluidic sample comprising the particles to a sensor active region on the depletion region by back grinding the substrate. Thus, material of the substrate may be removed so as to provide for a closer spatial relationship between the sensor active components of the sensor device and the fluidic analyte. Alternatively, it is possible to provide access of a fluidic sample comprising the particles to a sensor active region by implementing a silicon-on-nothing system. This may also refine the accuracy of the system.

The property of the depletion region may be a size of the depletion region. Without wishing to be bound to a specific theory, it is presently believed that the presence of charged particles in an environment of the depletion region or in functional contact therewith has an impact on the dimension of the depletion region. In turn, a change in size of the depletion region may have an impact on the electrical properties of the system formed by the doped regions and the depletion region, particularly having an influence on the breakdown voltage of the diode-like configuration. According to an exemplary embodiment of the invention, this phenomenon may be exploited as a sensor principle.

In the sensor device, the depletion region may have a concentration of charge carriers which is at least about 100 times, particularly at least about 1000 times, more particularly at least about 10000 times, smaller than a concentration of charge carriers in the first doped region and/or in the second doped region. With such ratios, it is possible to obtain a meaningful influence of the presence of charged particles on the electric measurement performed at or around the breakdown voltage of the sensor device.

Exemplary values for the doping doses in the regions p and n may be about $1E15\ cm^{-2}$, and $1E12\ cm^{-2}$ in the lowly doped region (n).

The second doped region may comprise a highly doped region ($n^+$) and a lowly doped region ($n^-$), wherein the lowly doped region is arranged adjacent to the first doped region ($p^+$) to create the depletion region at a junction with the first doped region. In such an embodiment, a dedicated region between the two oppositely highly doped regions is provided which may extend the length of the sensor active region as well, for instance allowing to increase the number of capture particles immobilizable on a surface of the sensor active region. In an alternative embodiment, the depletion region formed automatically for physical reasons between the two oppositely highly doped regions may be used as the depletion region. Such an embodiment may allow for a miniaturization of the sensor device.

One advantage of an exemplary embodiment of the invention over usual FET sensors is its sensitivity, since it works in the breakdown region of the diode, where a slight change in potential corresponds to a huge change in current. Simulations show that a change of 100 mV in the potential applied to the dielectric will give a difference of three orders of magnitude in the measured current and a change of 10 mV will give a difference of two orders of magnitude in the measured current.

The above embodiments are described in terms of n and p doping, but they can of course be inverted in a complementary device.

Exemplary applications of embodiments of the invention are chemical sensing, pH sensing, enzymatic sensing, DNA sensing, protein sensing. In conjunction with an electrochemical reaction it is possible to create some charge difference if necessary.

The sensor device may be a biosensor device, a chemical sensor device, a pH sensor device, an enzymatic sensor device, a DNA sensor device, a protein sensor device, or the like. Thus, embodiments of the invention can be implemented in very different technical fields.

Several sensors may be located close to each other, or integrated into the same substrate. The sensor active regions of several sensors may be located such as an array. The measurement of these sensors may be done at the same time, with the same detection unit. Statistical treatment may be applied to the data collected with these sensors.

The sensor chip may be manufactured in CMOS technology. CMOS technology, particularly the latest generations thereof, allow to manufacture structures with very small dimensions so that (spatial) accuracy of the device will be improved by implementing CMOS technology. A BiCMOS process in fact is a CMOS process with some additional processing steps to add bipolar transistors.

The sensor device may be monolithically integrated in a semiconductor substrate, particularly comprising one of the group consisting of a group IV semiconductor (such as silicon or germanium), and a group III-group V semiconductor (such as gallium arsenide).

The sensor chip or microfluidic device may be or may be part of a sensor device, a sensor readout device, a lab-on-chip, a sample transport device, a sample mix device, a sample washing device, a sample purification device, a sample amplification device, a sample extraction device or a hybridization analysis device. Particularly, the sensor or microfluidic device may be implemented in any kind of life science apparatus.

For any method step, any conventional procedure as known from semiconductor technology may be implemented. Forming layers or components may include deposition techniques like CVD (chemical vapour deposition), PECVD (plasma enhanced chemical vapour deposition), ALD (atomic layer deposition), or sputtering. Removing layers or components may include etching techniques like wet etching, plasma etching, etc., as well as patterning techniques like optical lithography, UV lithography, electron beam lithography, etc.

Embodiments of the invention are not bound to specific materials, so that many different materials may be used. For conductive structures, it may be possible to use metallization structures, silicide structures or polysilicon structures. For semiconductor regions or components, crystalline silicon may be used. For insulating portions, silicon oxide or silicon nitride may be used.

The biosensor may be formed on a purely crystalline silicon wafer or on an SOI wafer (Silicon On Insulator).

Any process technologies like CMOS, BIPOLAR, BICMOS may be implemented.

The aspects defined above and further aspects of the invention are apparent from the examples of embodiment to be described hereinafter and are explained with reference to these examples of embodiment.

BRIEF DESCRIPTION OF THE DRAWINGS

The invention will be described in more detail hereinafter with reference to examples of embodiment but to which the invention is not limited.

FIG. 1 illustrates a sensor device according to an exemplary embodiment of the invention.

FIG. 2 is a diagram showing an effect of an external potential applied on a dielectric on the current-voltage curve of the diode of FIG. 1.

FIG. 3 shows a cross-section of a conventional high voltage diode.

FIG. 4 shows a top view of the high voltage diode of FIG. 3.

FIG. 5 shows a conventional DIELER diode in a top view.

FIG. 6 shows a cross-section of the DIELER diode of FIG. 5 along a line B-B'.

FIG. 7 shows a cross-section of the DIELER diode of FIG. 5 along a line C-C'.

FIG. 12 to FIG. 14 show cross-sections of layer sequences providing liquid access by a system of back grinding of the wafer according to an exemplary embodiment of the invention.

FIG. 15 to FIG. 17 illustrate the fabrication of a silicon-on-nothing device according to an exemplary embodiment of the invention.

FIG. 18 to FIG. 21 show the use of the silicon-on-nothing system of FIGS. 15 to 17 to bring a liquid close to a detection electrode according to an exemplary embodiment of the invention.

DESCRIPTION OF EMBODIMENTS

Figure 8:
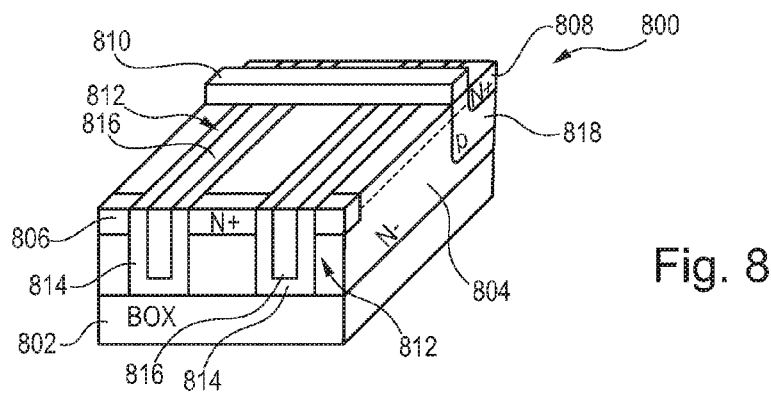
FIG. 8 shows a conventional DIELER device with field plates.

The illustration in the drawing is schematical. In different drawings, similar or identical elements are provided with the same reference signs.

Referring to FIG. 1, a sensor device 100 for detecting biological particles according to an exemplary embodiment of the invention will be explained.

The sensor device 100 comprises a silicon substrate 102. A p$^+$-doped region 104 is formed in a surface portion of the substrate 102 by a p-dopant implantation. A second doped region 106, namely an n$^+$-doped region, is formed in another surface portion of the substrate 102 by implanting an n-dopant of an n-type of conductivity which differs from the p-type of conductivity of the p$^+$-doped region 104.

Between the p$^+$-doped region 104 and the n$^+$-doped region 106, an optional lowly doped region 150 is formed in a surface portion of the substrate 102, which has an n$^-$-dopant concentration that is significantly smaller than the dopant concentrations in the first and second doped regions 104, 106. According to semiconductor physical laws, a depletion region 108 is formed at a junction between the two oppositely doped regions 104, 150. For an embodiment that omits the lowly doped region 150, reference is made to FIG. 28.

A sensor active region 110 is configured to influence a property of the depletion region 108 (or more precisely of the diode structure 104, 106, 108, 150), particularly a size of the depletion region 108 which may have an impact on a current-voltage correlation of the diode-like configuration, in the presence of electrically charged particles to be detected. As can be taken from FIG. 1, the sensing region 110 can be exactly on top of the depletion region 108.

A detection unit 112 is provided which may be a CPU (Central Processing Unit) or microprocessor which may be adapted to detect the particles based on an electric measurement performed upon application of a predetermined reference voltage between the first doped region 104 and the second doped region 106, the electric measurement being indicative of the presence of the particles in the sensor active region 110. The measurement may be performed at a predetermined reference voltage, particularly at a breakdown voltage estimated in the sample free state of the sensor device 100. It is possible to evaluate the breakdown voltage and the I(V) curves, which change when the size of the depletion region 108 changes. More particularly, the detection unit 112 is adapted to apply a predetermined reference voltage between the first doped region 104 and the second doped region 106 and to perform an electric measurement to detect the particles based on an evaluation of the electric measurement being sensitive to the property of the depletion region 108.

The sensor active region 110 is provided on or over the depletion region 108. The sensor active region 110 comprises capture particles 114 adapted for attachment with the particles to be detected. Furthermore, a dielectric layer 116 is provided between the capture particles 114 and the depletion region 108. The detection unit 112 controls the voltage V of a voltage source 120. Further, the detection unit 112 is in bidirectional communication with a current detector 122 or Amperemeter. The detection unit 112 is further coupled to an input/output unit 124. Via the input/output unit 124, a user may enter control commands or may receive detection results from the detection unit 112.

During operation, the detection unit 112 may be adapted for detecting the particles by first determining the predetermined voltage as a breakdown voltage of the diode formed by the first doped region 104 and the second doped region 106 in the absence of the particles. Then, the Amperemeter 122 at the breakdown voltage of the arrangement may measure an electric current in the absence of the particles. Subsequently, the Amperemeter 122 in the presence of the particles may measure the electric current. This measurement may be performed at the breakdown voltage of the arrangement determined beforehand in the absence of the particles. Subsequently, the detection unit 112 may compare the electric current values measured in the presence of the particles and in the absence of the particles, and may derive a sensor result therefrom.

Thus, a sensing device 100 is provided using a shift in the breakdown voltage of a reverse biased diode 104, 106, 108, 150.

The breakdown voltage of the pn diode 104, 106, 108, 150 in reverse bias is closely related to the size of the diode depletion region 108. The depletion region 108 size, and thus the breakdown voltage, can be increased by adding an optional lowly doped region 150 between the p$^+$ region 104 and the n$^+$ region 106. Furthermore, the breakdown voltage can be tuned by applying an external potential to this lowly doped region. Therefore, a change in the external potential on top of the lowly doped region 108 induced by the attachment of charged particles to the capture particles 114 will modify the breakdown voltage of the diode 104, 106, 108, 150.

According to an exemplary embodiment of the invention, the above-described effect may be used to detect the presence of charged particles. This will be described referring to FIG. 2.

FIG. 2 is a diagram 200 having an abscissa 202 along which the voltage is plotted in Volt. Along an ordinate 204, the current is plotted in Ampere. The voltage $V_{BDO}$ is shown as well in FIG. 2 for the diode 104, 106, 108, 150 of FIG. 1. When the voltage at the dielectric layer 116 is 0 Volt, a characteristic curve 206 is measured. When the voltage $V_{diel}$ at the dielectric layer 116 is −100 mV, a second curve 208 is measured. As can be taken from FIG. 2, after attachment and before attachment of charged particles to the capture particles 114, the current value at the voltage $V_{BDO}$ significantly differs (compare $I_{after}$, $I_{before}$).

Before the application of the charged particles, a first measurement 206 determines a voltage $V_{BD0}$, close the breakdown voltage of the diode 104, 106, 108, 150 and where the current increases a lot as a function of the potential, and measures the current at $V_{BD0}$. After the application of the charged particles, a second measurement 208 determines the current also at $V_{BD0}$. Because the measurements occur in the range of the breakdown voltage, the simulations show that the difference in the current between both measurements can be of several orders of magnitude.

In the following, some basic recognitions of the present inventors will be explained based on which exemplary embodiments of the invention have been developed.

Even if a sensor according to an exemplary embodiment of the invention is clearly not a high-voltage device, the high-voltage devices are a background of the invention because a sensor according to an exemplary embodiment of the invention makes use of the techniques (lowly-doped region, modification of the size of the depletion region by an external potential) that are used in their field.

A main challenge in high voltage devices is to make diodes that can withstand a high voltage difference without breakdown. This increase in the breakdown voltage is often achieved by integrating a large lowly doped drift region between the p-type and n-type regions, see FIG. 3, FIG. 4.

FIG. 3 shows a cross-sectional view 300 of a conventional diode having a substrate 302, a p$^+$-region 304, an n$^+$-region 306 and an n$^-$-doped region 308.

FIG. 4 shows a plan view 400 of the diode of FIG. 3.

If the dimensions and doping of the region 308 are adequately tuned, this increase in the breakdown voltage can be enhanced by the RESURF effect. Furthermore, applying a potential to the n-region may further modify the breakdown voltage of the diode.

DIELER diodes are disclosed as such in WO 2006/136979. Trenches filled with an isolator and located as shown in FIG. 5 to FIG. 7 will increase further the breakdown voltage of the diode. An alternative to the DIELER is to only partially fill the trenches with oxide and thus create conducting field plates in the trenches.

FIG. 5 shows a top view 500 of a DIELER diode 500. As compared to FIG. 4, a plurality of trenches 502 is provided.

FIG. 6 shows a cross-sectional view 600 along a line B-B' of FIG. 5, and FIG. 7 shows a cross-sectional view 700 along a line C-C' of FIG. 5.

FIG. 8 shows a three-dimensional view 800 of a conventional DIELER diode 800. A buried oxide layer 802 is shown. An n$^-$-external drain region 804 is provided thereon.

A first n+ source/drain region 806 and a second n+ source/drain region 808 are shown. Furthermore, a gate 810 is shown. Trenches 812 are formed having a dielectric layer 814 and an electrically conductive field plate 816. Furthermore, a p-well 818 is shown.

Figure 9:
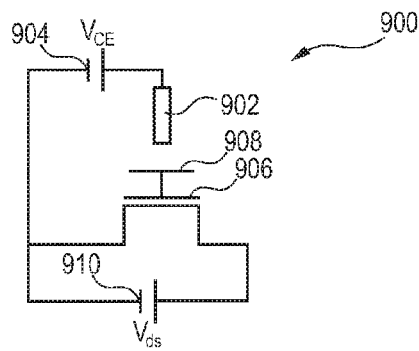
FIG. 9 shows a conventional FET sensor.

FIG. 9 shows a conventional FET sensor 900. A counter electrode 902 is coupled to a voltage source $V_{CE}$ 904, which voltage source is further coupled to a transistor 906 having a gate being coupled to a detection electrode 908. A further voltage source 910 $V_{ds}$ is shown as well.

A lot of the FET sensors are built in the same way like shown in FIG. 9. The liquid containing the species to detect is in contact with the counter electrode 902 (sometimes called reference electrode) and a detection electrode 908. The detection electrode 908 is connected to the gate of the transistor 906. Several detection systems exist to detect different events, like pH changes in the solution, or attachment of biological particles, but all have in common that they result in a change in the gate potential of the transistor. This change in the gate potential induces a change in the source/drain current of the transistor.

To summarize, the detection of an event resulting in a change in the gate potential is made by a measurement in a change of the source/drain current.

In the following, an embodiment of the invention having a DIELER diode with field plates will be explained.

Figure 10:
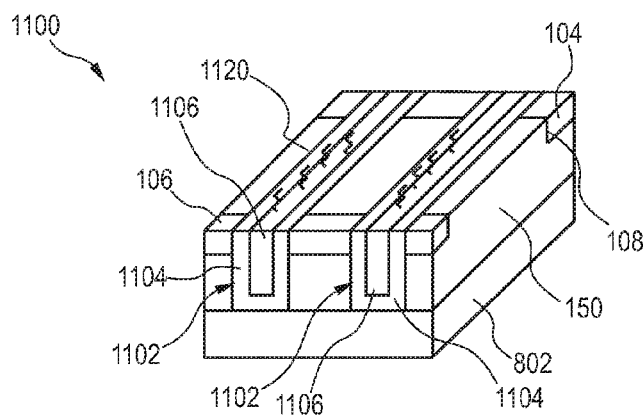
FIG. 10 shows a sensor device according to another exemplary embodiment of the invention.

FIG. 10 shows a sensor device 1100 according to an exemplary embodiment of the invention.

The sensor device 1100 comprises a plurality of trenches 1102 filled partially with dielectric material 1104 and extending from the first doped region 104 via the lowly-doped region 108 to the second doped region 106. The sensor device 1100 comprises an electrically conductive inlay 1106 in the dielectric material 1104 of the plurality of trenches 1102. The trenches 1102 are part of the sensor active region 110.

FIG. 10 shows a scenario in which particles to be detected 1120 are provided functionally coupled to the field plates 1106.

Figure 11:
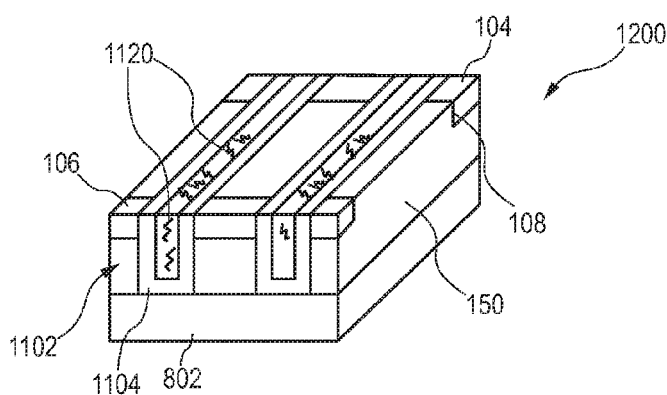
FIG. 11 shows a sensor device according to another exemplary embodiment of the invention.
Figure 22:
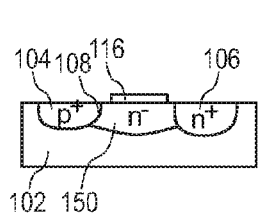
FIG. 22 to FIG. 25 show cross-sections of a layer sequence during DNA sensing according to an exemplary embodiment of the invention.

In the sensor device 1200 according to another exemplary embodiment of the invention shown in FIG. 11, the particles 1120 are provided within the trenches 1102.

The charged particles 1120 to detect can either be on top of fields plates 1106 (FIG. 10) or the STI 1104 can be empty and the charged particles 1120 come in the place of the field plates 1106 (see FIG. 11). There, the area coverage by the external potential induced by the charge attached will even be larger than with the "basic" diode. Thus a higher difference in the breakdown voltage may be possible.

The embodiment of FIG. 1 (simple diode) is very easy to build with doping a piece of monocrystalline silicon or by using the technology of high-voltage CMOS.

Taking into account the fact that the liquid should not be in contact with the electrical connections, several solutions for this problem are possible. It is possible to give to the liquid a direct access to the detection electrode or to build the interconnect structure of the circuit and to have the electrode included in this interconnect structure.

Alternatively, back grinding of the wafer is possible, see FIG. 12 to FIG. 14, in which the embedded p-region 1402 can be there or not.

FIG. 12 shows a cross-sectional view 1400 of a layer sequence according to an exemplary embodiment of the invention.

The layer sequence 1400 includes a further p-conductive layer 1402 below an interconnect structure 1404 which includes contacts 1406, 1408 to the first and second doped regions 104, 106, respectively. Thus, FIG. 12 shows a wafer with an interconnect structure.

FIG. 13 shows a layer sequence 1500, in which the wafer 102 is grinded to provide liquid access.

FIG. 14 shows a layer sequence 1600, in which an oxide layer 1602 is created, and charged particles 1604 are deposited thereon.

Further alternatively, "silicon on nothing" vias may be implemented. This embodiment may use a silicon-on-nothing method, like the one shown in FIG. 15 to FIG. 17.

FIG. 15 shows an image 1700 regarding spherical ESS.

An image 1800 shown in FIG. 16 relates to pipe shaped ESS.

An image 1900 shown in FIG. 17 relates to plate shaped ESS.

Regarding FIG. 15 to FIG. 17, reference is made to T. Sato et al., Japanese Journal of Applied Physics Part 1—Regular Papers Short Notes & Review Papers 43, 12 (2004), for a more detailed explanation.

FIG. 18 to FIG. 21 illustrate the use of a silicon-on-nothing system to bring the liquid close to the detection electrode. Thus, FIG. 18 to FIG. 21 show the fabrication of a silicon-on-nothing device 2300.

As can be taken from FIG. 18, a hole 2000 is formed in the substrate 102.

An interconnect structure 1404 is then formed, as can be taken from FIG. 19. As can be taken from FIG. 20, vias 2200 are etched, and a silicon oxide layer 1602 is created in the hole 2000. FIG. 21 then shows a liquid motion direction 2302.

A sensor according to an exemplary embodiment of the invention is capable to measure the difference between two situations: a reference situation and detection itself.

1) In the reference situation, no liquid or a reference liquid is put on the dielectric, the reference curve $I^0(V)$ of the reversed diode is measured and the breakdown potential $V_{BD0}$ is determined. The manufacturer may do such a reference measurement and the result may be provided to the customer.

2) The detection itself may be performed after the deposition of the liquid to test on the detection electrode. The measurement can either be a scan that provides a curve I(V) to compare to the reference curve $I^0(V)$, or just a measurement of the current at a potential close to $V_{BD0}$.

Because the potential with the highest difference of current is between breakdown potentials of the situations with no particles and with a lot of particles (see FIG. 2) it is also possible to do a pre-test to get an idea of this ideal potential and then do the real measurement. The currents obtained in the simulations are so low (for instance $<10^{-5}$A) that the breakdown should not destroy the diode.

The measurement protocol may be the following:

a) Measurement of the curve I(V) with a reference liquid, determination of $V_{BD0}$. b) Measurement with a solution highly concentrated in particles, determination of $V_{BD1}$.

c) Measurement of the current with a probe particle at a potential in the middle of $V_{BD0}$ and $V_{BD1}$. With this measurement, one may know which electrode in the array is functionalized by the probe particle. The point of the whole experiment is actually to detect the presence or absence of the target particle complementary of this one.

d) Measurement with the target particle. If it is not complementary to the other, it will not attach it and measurement c) and d) will give the same result. If it attaches, its presence may modify the current at the voltage.

FIG. 22 to FIG. 25 illustrate an exemplary embodiment of particles sensing, these particles being DNA.

Figure 23:
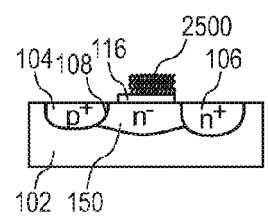
Figure 24:
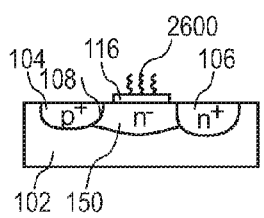
Figure 25:
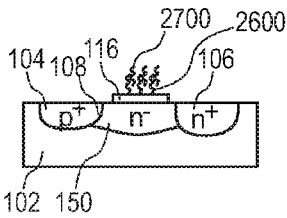

In FIG. 23, a solution with highly concentrated DNA 2500 is measured. In FIG. 24, a measurement with known strand of DNA 2600 is performed. In FIG. 25, attachment between the strands 2600 and test DNA 2700 occurs.

Figure 28:
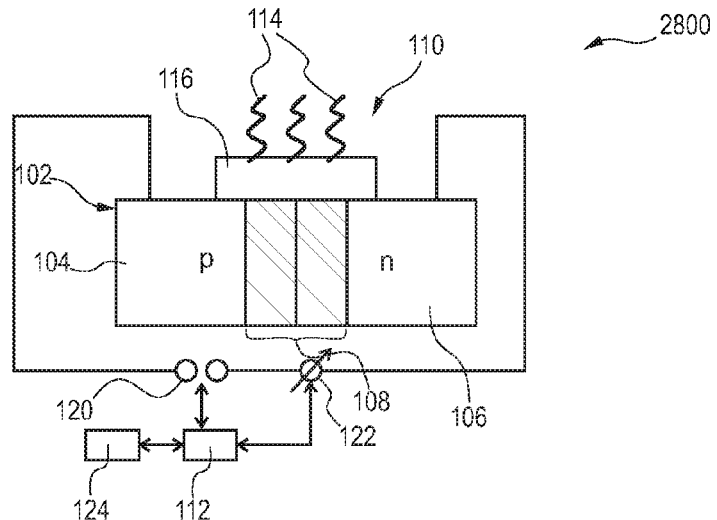
Figure 29:
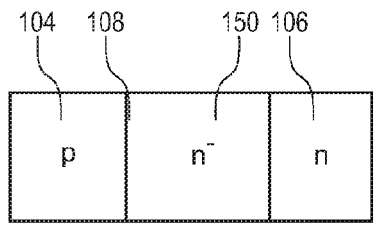
Figure 30:
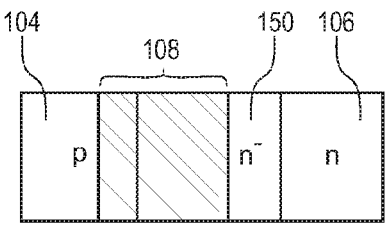

Referring to FIG. 28, a sensor device 2800 for detecting biological particles according to a preferred embodiment of the invention will be explained.

FIG. 26, FIG. 27, FIG. 29 and FIG. 30 illustrate layer sequences used for explaining a working principle of the sensor device 2800, which is shown in FIG. 28.

The embodiment of FIG. 28 omits the central lowly-doped region n⁻ 150 of FIG. 1.

Figure 26:
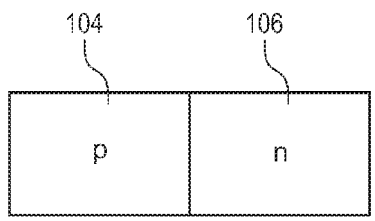
FIG. 26, 27, 29, 30 illustrate layer sequences used for explaining a sensor device according to a preferred embodiment of the invention, which is shown in FIG. 28.
Figure 27:
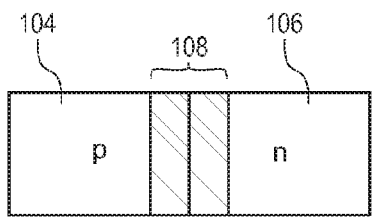

As can be taken from FIG. 26 and FIG. 27, a diode is formed of a p-doped region 104 and an n-doped region 106. The fact that these regions 104, 106 are in contact with each other creates at their junction a depletion region 108. The breakdown voltage of the diode depends on the size of this depletion region 108.

The principle of the embodiment of FIG. 28 can work with such a diode (i.e, a diode without lowly-doped region 150 in the middle, compare FIG. 1) since the presence of particles may influence the size of the depletion region 108 and thus the breakdown voltage of the diode. FIG. 28 shows that the central lowly-doped region 150 is not needed.

The breakdown voltage depends on the size of the depletion region 108 which in turn depends on the doping concentration. Therefore, a way to increase the breakdown voltage of a diode is to add a lowly doped region 150 (n⁻ for example but it can be p⁻) between the p and n regions 104, 106, see FIG. 1, FIG. 29, FIG. 30. In that case, the depletion region 108 will be localized at the junction between the p and n regions 104, 150 and it may extend more in the n⁻ region 150 than in the p region 104 (see FIG. 30). It may sometimes be so large that it extends to the n region 106.

Advantages of the embodiment of FIG. 1 with a central lowly-doped region 150 are:

the depletion region 108 size and thus the breakdown voltage can be tuned more easily by changing the doping and size of the middle region 150, and since the depletion region 108 is larger, the particles have more place to attach, so more particles can attach and the detection may be easier. Finally, it should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The words "comprising" and "comprises", and the like, do not exclude the presence of elements or steps other than those listed in any claim or the specification as a whole. The singular reference of an element does not exclude the plural reference of such elements and vice-versa. In a device claim enumerating several means, several of these means may be embodied by one and the same item of software or hardware. The mere fact that certain measures are recited in mutually different dependent claims does not indicate that a combination of these measures cannot be used to advantage.

The invention claimed is:

1. A sensor device for detecting particles, the sensor device comprising:
    a substrate;
    a first doped region formed in the substrate by a first dopant of a first type of conductivity;
    a second doped region formed in the substrate by a second dopant of a second type of conductivity which differs from the first type of conductivity, wherein the second doped region includes a lower doped region of the second conductivity type and a higher doped region of the second conductivity type;
    a depletion region at a junction between the first doped region and the second doped region, wherein the lower doped region is adjacent to the first doped region and located between the first doped region and the higher doped region;
    a sensor active region configured and arranged to influence a property of the depletion region in the presence of the particles; and
    a detection circuit configured and arranged to detect the particles based on an electric measurement performed upon application of a predetermined reference voltage between the first doped region and the second doped region, the electric measurement being indicative of current passing through the depletion region while the presence of the particles in the sensor active region influence the current passing through the depletion region.

2. The sensor device according to claim 1, wherein
    a substrate configured and arranged to receive a sample, in the form of a liquid or solid substance, in an aperture of the substrate;
    wherein the sensor active region is configured and arranged to access the sample in the aperture and influence the property of the depletion region in the presence of the particles; and
    the first doped region is a p-doped region and the second doped region is an n-doped region.

3. The sensor device according to claim 1, wherein
    the sensor active region is configured and arranged to influence a value of a breakdown voltage of an arrangement formed by the first doped region, the second doped region and the depletion region in the presence of the particles.

4. The sensor device according to claim 1, wherein
    the substrate includes a dopant having the first conductivity type; and
    the sensor active region comprises capture-particles configured and arranged for attaching with the particles.

5. The sensor device according to claim 4, wherein the sensor active region comprises a dielectric layer between the capture particles and the depletion region.

6. The sensor device according to claim 1, wherein the detection circuit is configured and arranged to detect the particles by performing the electric measurement at or around a breakdown voltage, as the predetermined reference voltage, of an arrangement formed by the first doped region, the second doped region and the depletion region.

7. The sensor device according to claim 1, wherein the detection circuit is configured and arranged for operating an arrangement formed by the first doped region, the second doped region and the depletion region with a reverse bias.

8. The sensor device according to claim 1, wherein the detection circuit is configured and arranged to detect the particles based on a shift of a breakdown voltage of an arrangement formed by the first doped region, the second doped region and the depletion region with a reverse bias.

9. The sensor device according to claim 1, wherein the detection circuit is configured and arranged to detect the particles by:
    determining the predetermined reference voltage as a breakdown voltage of an arrangement formed by the first doped region, the second doped region and the depletion region in the absence of the particles;

measuring an electric current at the breakdown voltage of the arrangement in the absence of the particles;

measuring, in the presence of the particles, an electric current passing through the depletion region at the breakdown voltage of the arrangement determined in the absence of the particles; and comparing the electric current measured in the presence of the particles and in the absence of the particles.

10. The sensor device according to claim 1, configured and arranged to detect electrically charged particles.

11. The sensor device according to claim 1, wherein the substrate comprises a plurality of trenches filled at least partially with dielectric material and extending from the first doped region to the second doped region.

12. The sensor device according to claim 11, comprising an electrically conductive inlay in the dielectric material of at least a part of the plurality of trenches.

13. The sensor device according to claim 11, wherein the plurality of trenches is part of the sensor active region.

14. The sensor device according to claim 2, configured and arranged in that the sample including the particles is free from a contact with electrical connections of the sensor device.

15. The sensor device according to claim 1, wherein the property is a size of the depletion region.

16. The sensor device according to claim 1, wherein the depletion region has a concentration of charge carriers which is one of: at least $10^2$ times, at least $10^3$ times, and at least $10^4$ times smaller than a concentration of charge carriers in the first doped region and/or in the second doped region.

17. A sensor device for detecting particles, the sensor device comprising:

a substrate;

a first doped region formed in the substrate by a first dopant of a first type of conductivity;

a second doped region formed in the substrate by a second dopant of a second type of conductivity which differs from the first type of conductivity, wherein the second doped region comprises a highly doped region and a lowly doped region;

a depletion region at a junction between the first doped region and the second doped region, wherein the lowly doped region is arranged adjacent to the first doped region to form the depletion region at the junction with the first doped region;

a sensor active region configured and arranged to influence a property of the depletion region in the presence of the particles; and a detection circuit configured and arranged to detect the particles based on an electric measurement performed upon application of a predetermined reference voltage between the first doped region and the second doped region, the electric measurement being indicative of current passing through the depletion region while the presence of the particles in the sensor active region influence the current passing through the depletion region.

18. The sensor device according to claim 17, wherein the sensor active region is provided directly on the depletion region.

19. The sensor device according to claim 1, configured and arranged as one of a biosensor device, a chemical sensor device, a pH sensor device, an enzymatic sensor device, a DNA sensor device, and a protein sensor device.

20. A method of detecting particles, the method comprising:

providing a depletion region at a junction between a first doped region formed in a substrate by a first dopant of a first type of conductivity and a second doped region formed in the substrate by a second dopant of a second type of conductivity which differs from the first type of conductivity, wherein the second doped region includes a lower doped region and a higher doped region, and the lower doped region is adjacent to the first doped region and located between the first doped region and the higher doped region;

providing access of a fluidic sample comprising the particles to a sensor active region on the depletion region by back grinding the substrate;

influencing a property of the depletion region by the presence of the particles; and detecting the particles based on an electric measurement performed upon application of a predetermined reference voltage between the first doped region and the second doped region, the electric measurement being indicative of the presence of the particles in the sensor active region.

21. The method according to claim 20, further comprising providing access of a fluidic sample comprising the particles to a sensor active region by implementing a silicon-on-nothing system.

22. The sensor device according to claim 1, wherein the first and second doped regions have a higher doping concentration than the substrate.

* * * * *